(12) United States Patent
Tsuda et al.

(10) Patent No.: US 8,071,793 B2
(45) Date of Patent: Dec. 6, 2011

(54) MACROLIDE COMPOUND

(75) Inventors: Masashi Tsuda, Sapporo (JP); Keiko Oguchi, Sapporo (JP); Rie Iwamoto, Sapporo (JP); Yumiko Okamoto, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 200 days.

(21) Appl. No.: 12/448,633

(22) PCT Filed: Dec. 19, 2007

(86) PCT No.: PCT/JP2007/001425
§ 371 (c)(1), (2), (4) Date: Jun. 26, 2009

(87) PCT Pub. No.: WO2008/081568
PCT Pub. Date: Jul. 10, 2008

(65) Prior Publication Data
US 2010/0121079 A1    May 13, 2010

(30) Foreign Application Priority Data
Dec. 27, 2006   (JP) .............................. 2006-351043

(51) Int. Cl.
*C07D 321/00* (2006.01)
*C07D 493/00* (2006.01)
*C07D 313/04* (2006.01)

(52) U.S. Cl. ..................................... 549/267; 549/270

(58) Field of Classification Search .................. 549/267, 549/270, 271
See application file for complete search history.

(56) References Cited

OTHER PUBLICATIONS

Kobayashi et al. Tetrahedron Letters, 27(47), 5755-5758, 1986.*
Masashi Tsuda, et al., "Amphidinolide U, Novel 20-Membered Macrolide from Marine . . . ", Tetrahedron 55, 1999, pp. 14565-14570, Elsevier Science Ltd.
Masashi Tsuda et al., "Iriometeolides -1b and -1c, 20-Membered Macrolides from a Marine . . . ", Journal of Natural Products, 2007, pp. 1661-1663, American Chemical Society.
Junichi Kobayashi et al., "Amphidinolide-A, A Novel Antineoplastic Macrolide from the Marine . . . ", Tetrahedron Letter, pp. 5755-5758, vol. 27, No. 47, Pergamon Journals, Ltd.
"Amphidinolides B6 and B7, Cytotoxic Macrolides . . . " written by K. Oguchi et al. in Journal Of Natural Products, vol. 70, No. 10, 2007, pp. 1676-1679.
"Iriomoteolide-1 a, a Potent Cytotoxic 20-Membered Macrolide . . . " written by M. Tsuda et al. in Journal Of Organic Chemistry, vol. 72, No. 12, 2007, pp. 4469-4474.
"Amphidinolides T2, T3, and T4, new 19-membered macrolides . . . " written by Kobayashi Jun-Ichi et al. In Journal Of Organic Chemistry, vol. 66, No. 1,1, Jan. 2001, pp. 134-142.

* cited by examiner

*Primary Examiner* — Nizal Chandrakumar
(74) *Attorney, Agent, or Firm* — DLA Piper LLP (US)

(57) ABSTRACT

Disclosed are: a novel *dinoflagellate* alga; and a macrolide compound which can be used as a novel anticancer agent. Specifically disclosed is a macrolide compound produced by a *dinoflagellate Amphidinium* sp. Strain HYA002 or HYA0024. The macrolide compound has excellent proliferation-inhibiting effect against a human tumor cell and therefore can be used as a novel anticancer agent.

3 Claims, No Drawings

MACROLIDE COMPOUND

TECHNICAL FIELD

The present invention relates to a novel macrolide compound, an anticancer agent with the macrolide compound as an active ingredient and a method for producing the macrolide compound. This invention pertains to a patent application regarding the results of an entrusted research by the Japan's national government and other organizations (effective promotion of a joint research by industrial, academic and government sectors, "Miriyobisaimo karano yuyokagakusozai no tansaku to kaihatsu (Seeking and development of useful chemical materials from unused microalgae)" financed by 2006 Special Coordination Funds for the Promotion of Science and Technology sponsored by the Ministry of Education, Culture, Sports, Science and Technology in compliance with Article 30 of the Act on Special Measures concerning Industrial Revitalization).

BACKGROUND ART

A variety of compounds constituting anticancer agents are currently developed by examining a derivation and a chemical structure thereof. Amid a growing demand for such new anticancer agents, anticancer agent development is constantly required due to such problems as side effects of an anticancer agent, generation of drug-resistant cancer cells caused by long-term use of anticancer agents and different medicinal effects by the type of cancer.

In fact, seaweed or unicellular algae is known as a natural resource required for providing an anticancer agent or candidate compounds thereof. A macrolide compound produced by *dinoflagellate* alga (Amphidinolide) particularly receives much academic attention due to a strong antitumor activity (Non-patent document 1). Because of the above-mentioned problems, however, seeking and development of anticancer agents, marine organism-derived antitumor substances in particular, is always regarded as a crucially important issue.

[Non-patent document 1] J. Kobayashi, et. al., teterahedron Lett., Vol. 27, p 5755, 1986

DISCLOSURE OF THE INVENTION

Problem to be Solved

The aim of the present invention is to provide a novel anticancer agent and a novel *dinoflagellate* alga strain that produces the novel anticancer agent, by searching for an excellent *dinoflagellate* alga-derived antitumor substance.

The inventors found out a tumor cell proliferation-inhibiting effect of a novel macrolide compound produced by a novel *dinoflagellate* alga by isolating a strain of the novel *dinoflagellate* alga from a natural environment, which is usable as an anticancer agent, and completed each of the following inventions.

1) A compound consisting of at least one of following general Formula 1, Formula 2, Formula 3, Formula 4 and Formula 5 and salts thereof:

[Compound 1]

Formula 1

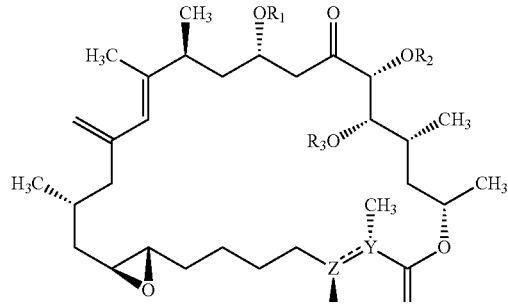

[Compound 2]

Formula 2

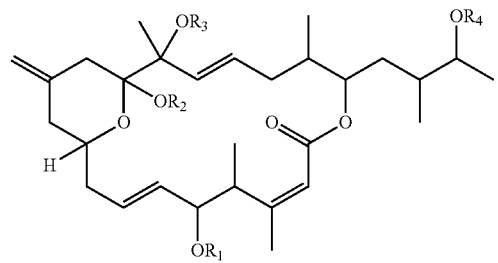

[Compound 3]

Formula 3

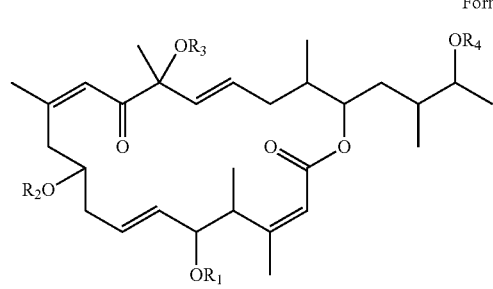

[Compound 4]

Formula 4

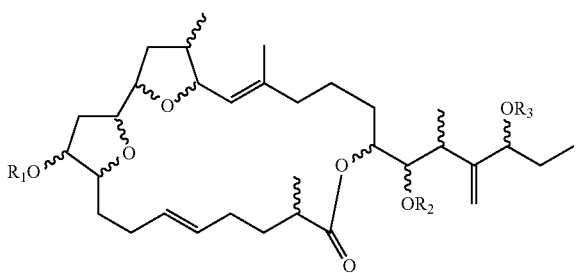

[Compound 5]

Formula 5

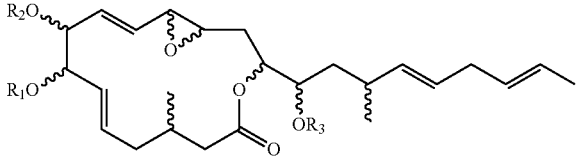

wherein $R_1$, $R_2$, $R_3$ and $R_4$ are respectively one selected from hydrogen group and oxygen protecting group; Z-Y is one selected from a carbon single bond and a carbon double bond; and wherein, when Z-Y is a carbon single bond, X is hydroxy group, and when Z-Y is a carbon double bond, X is hydrogen.

2) An anticancer agent containing at least one of compounds according to 1) as an active ingredient.

3) A method for producing any one of compounds according to 1), comprising a process for culturing an *Amphidinium* sp. Strain HYA002 as a *dinoflagellate* alga, and a process for collecting at least one of compounds according to 1) from a culture.

4) A method for producing any one of compounds according to 1), comprising a process for culturing an *Amphidinium* sp. Strain HYA024 as a *dinoflagellate* alga, and a process for collecting at least one of compounds according to 1) from a culture.

5) An *Amphidinium* sp. Strain HYA002 as a *dinoflagellate* alga.

6) An *Amphidinium* sp. Strain HYA024 as a *dinoflagellate* alga.

Advantageous Effect of the Invention

A macrolide compound of this invention has an excellent proliferation-inhibiting effect against a human tumor cell and therefore can be used as a novel anticancer agent.

BEST MODE FOR CARRYING OUT THE INVENTION

A macrolide compound of this invention is a compound having an antitumor activity produced by a novel strain of *Amphidinium* sp. as *dinoflagellate* alga and having a chemical structure represented by any one of the following Formulae 1 to 5:

[Compound 6]

Formula 1

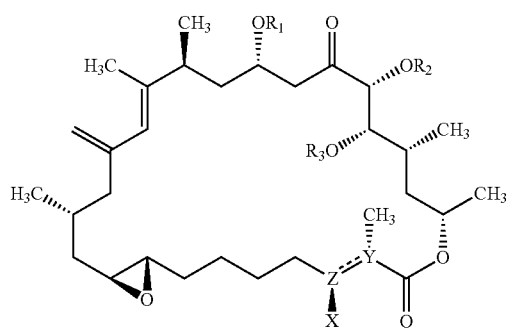

[Compound 7]

Formula 2

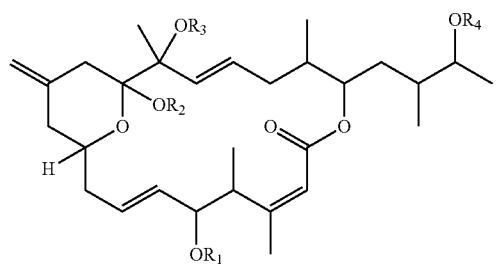

[Compound 8]

Formula 3

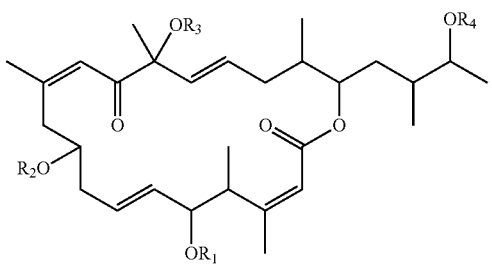

[Compound 9]

Formula 4

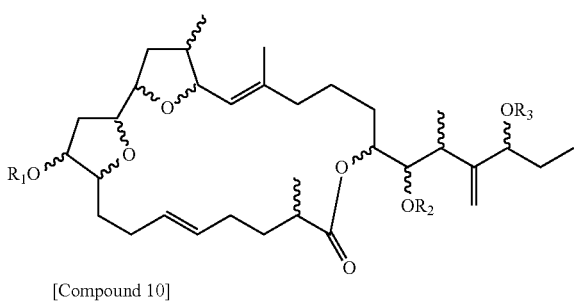

[Compound 10]

Formula 5

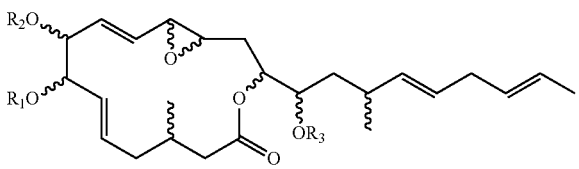

werein $R_1$, $R_2$, $R_3$ and $R_4$ are respectively one selected from hydrogen group and oxygen protecting group; Z-Y is one selected from a carbon single bond and a carbon double bond; and wherein, when Z-Y is a carbon single bond, X is hydroxy group, and when Z-Y is a carbon double bond, X is hydrogen.

Particularly preferred embodiments of each of the compounds represented by Formulae 1 to 5 are given by the following Formulae 6 to 11.

a) A compound represented by Formula 6: $R_1$, $R_2$, $R_3$ are each hydrogen, Z-Y is single bond and X is hydroxy group in Formula 1.

[Compound 11]

Formula 6

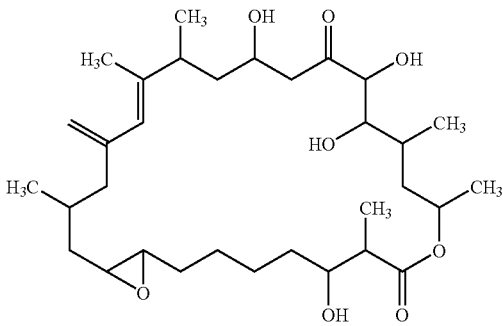

Form: colorless oil, solubility: soluble in alcohol, chloroform, ethyl acetate and acetone, insoluble in hexane and water, molecular weight measurement: m/z 567 (M+H)$^+$, $^1$H-NMR spectrum (600 MHz in deuterated chloroform) δ 0.86 (3H, d, 6.5 Hz, H$_3$-28), 1.06 (3H, d, 6.8 Hz, H$_3$-31), 1.06 (3H, d, 6.8 Hz, H$_3$-32), 1.11 (1H, m, H-10), 1.12 (3H, d, 6.7 Hz, H$_3$-27), 1.13 (1H, m, H-7), 1.20 (1H, m, H-24), 1.22 (3H, d, 6.7 Hz, H$_3$-26), 1.32 (1H, m, H-6), 1.34 (1H, m, H-4), 1.40 (1H, ddd, 4.3, 9.7, 14.0 Hz, H-17), 1.48 (1H, m, H-10), 1.50 (1H, m, H-5), 1.51 (1H, m, H-4), 1.54 (1H, m, H-6), 1.61 (1H, m, H-5), 1.63 (1H, m, H-11), 1.74 (3H, brs, H$_3$-30), 1.79 (1H, m, H-12), 1.79 (1H, m, H-24), 1.83 (1H, m, H-17), 1.88 (1H, m, H-7), 1.90 (1H, m, H-23), 2.13 (1H, dd, 4.2, 13.3 Hz, H-12), 2.18 (1H, ddq, 4.3, 11.4, 6.6 Hz, H-16), 2.45 (1H, dq, 7.2, 7.0 Hz, H-2), 2.54 (1H, dd, 1.8, 15.7 Hz, H-19), 2.71 (1H, dt, 9.1, 2.4 Hz, H-8), 2.73 (1H, dd, 9.7, 15.7 Hz, H-19), 2.87 (1H, dt, 9.3, 2.4 Hz, H-9), 3.69 (1H, brd, 9.4 Hz, H-22), 3.76 (1H, dt, 1.5, 7.2 Hz, H-3), 4.01 (1H, ddt, 1.8, 4.0, 9.7 Hz, H-18), 4.46 (1H, brs, H-21), 4.82 (1H, brs, H-29), 5.00 (1H, brs, H-29), 5.18 (1H, ddq, 1.3, 12.2, 7.4 Hz, H-25), 5.48 (1H, s, H-14), $^{13}$C-NMR spectrum (150 MHz in deuterated chloroform) δ 12.7 (CH$_3$, C-30), 14.2 (CH$_3$, C-27), 16.2 (CH$_3$, C-32), 17.9 (CH$_3$, C-28), 20.5 (CH$_3$, C-31), 21.2 CH$_3$, C-26), 24.9 (CH$_2$, C-5), 25.1 (CH$_2$, C-6), 29.3 (CH, C-11), 32.2 (CH$_2$, C-7), 32.4 (CH, C-23), 33.5 (CH$_2$, C-4), 40.2 (CH$_2$, C-24), 40.6 (CH$_2$, C-10), 40.7 (CH$_2$, C-17), 41.2 (CH, C-16), 44.6 (CH$_2$, C-19), 47.0 (CH$_2$, C-12), 48.2 (CH, C-2), 58.6 (CH, C-9), 60.0 (CH, C-8), 67.2 (CH, C18), 67.7 (CH, C-25), 71.2 (CH, C-3), 74.7 (CH, C-22), 77.9 (CH, C-21), 114.9 (CH$_2$, C-29), 126.3 (CH, C-14), 141.5 (C, C-15), 144.1 (C, C-13), 177.4 (C, C-1), 209.9 (C, C-20)

b) A compound represented by Formula 7: $R_1$, $R_2$ and $R_3$ are each hydrogen, Z-Y is double bond and X is hydrogen in Formula 1.

[Compound 12]

Formula 7

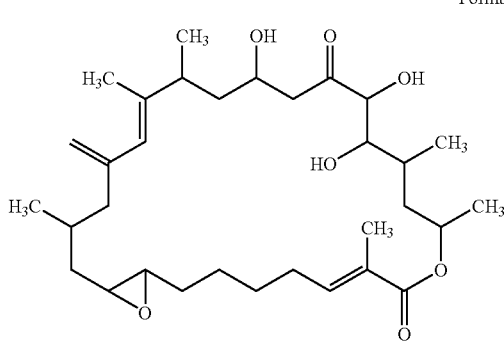

Solubility: soluble in alcohol, chloroform, ethyl acetate and acetone, insoluble in hexane and water, molecular weight measurement: m/z 549 (M+H)$^+$, $^1$H-NMR spectrum (600 MHz in deuterated chloroform) δ 0.86 (3H, d, 6.5 Hz, H$_3$-28), 1.01 (3H, d, 6.7 Hz, H$_3$-32), 1.05 (3H, d, 6.7 Hz, H$_3$-31), 1.13 (1H, m, H-10), 1.15 (1H, m, H-7), 1.24 (1H, m, H-24), 1.26 (3H, d, 6.7 Hz, H$_3$-26), 1.42 (1H, m, H-6), 1.42 (1H, m, H-17), 1.43 (1H, m, H-5), 1.50 (1H, m, H-10), 1.56 (1H, m, H-5), 1.60 (1H, m, H-6), 1.61 (1H, m, H-11), 1.73 (3H, brs, H$_3$-30), 1.78 (1H, m, H-12), 1.80 (3H, brs, H$_3$-27), 1.80 (1H, m, H-17), 1.83 (1H, m, H-7), 1.90 (1H, m, H-24), 1.93 (1H, m, H-23), 2.13 (1H, dd, 4.0, 13.5 Hz, H-12), 2.16 (1H, m, H-4), 2.20 (1H, m, H-16), 2.28 (1H, m, H-4), 2.54 (1H, brd, 15.6 Hz, H-19), 2.73 (1H, dd, 9.0, 15.6 Hz, H-19), 2.74 (1H, dt, 9.0, 2.4 Hz, H-8), 2.91 (1H, dt, 9.5, 2.4 Hz, H-9), 3.69 (1H, brd, 9.0 Hz, H-22), 3.97 (1H, bRt, 8.5 Hz, H-18), 4.43 (1H, brs, H-21), 4.81 (1H, brs, H-29), 5.00 (1H, brs, H-29), 5.06 (1H, m, H-25), 5.50 (1H, s, H-14), 6.88 (1H, bRt, 7.0 Hz, H-3), $^{13}$C-NMR spectrum (150 MHz in deuterated chloroform) δ 12.3 (CH$_3$, C-27), 12.6 (CH$_3$, C-30), 15.7 (CH$_3$, C-32), 17.6 (CH$_3$, C-28), 20.3 (CH$_3$, C-31), 21.2 (CH$_3$, C-26), 25.3 (CH$_2$, C-5), 27.9 (CH$_2$, C-4), 28.0 (CH$_2$, C-6), 29.0 (CH, C-11), 32.1 (CH$_2$, C-7), 32.5 (CH, C-23), 40.0 (CH$_2$, C-24), 40.3 (CH$_2$, C-17), 40.5 (CH$_2$, C-10), 41.1 (CH, C-16), 44.7 (CH$_2$, C-19), 47.1 (CH$_2$, C-12), 58.3 (CH, C-9), 60.0 (CH, C-8), 67.0 (CH, C18), 68.0 (CH, C-25), 75.1 (CH, C-22), 77.4 (CH, C-21), 114.9 (CH$_2$, C-29), 126.2 (CH, C-14), 127.8 (C, C-2), 141.5 (C, C-15), 141.8 (CH, C-3), 144.0 (C, C-13), 167.8 (C, C-1), 210.8 (C, C-20)

c) A compound represented by Formula 8: $R_1$, $R_2$, $R_3$ and $R_4$ are each hydrogen in Formula 2.

[Compound 13]

Formula 8

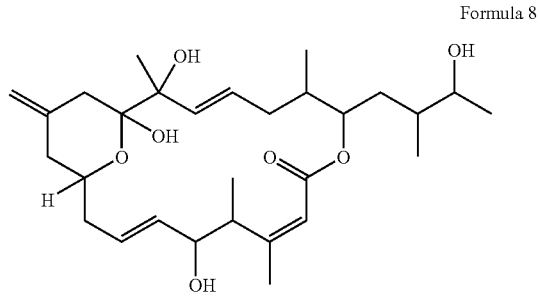

Form: colorless solid, solubility: soluble in chloroform, acetone, ethyl acetate, ethanol and methanol, insoluble in water and hexane, molecular weight measurement: m/z 529.2 (M+Na)$^+$, $^1$H-NMR spectrum (600 MHz in deuterated chloroform) δ 0.91 (3H, d, 6.7 Hz, H$_3$-29), 0.99 (3H, d, 6.8 Hz, H$_3$-28), 1.11 (3H, d, 6.3 Hz, H$_3$-23), 1.24 (3H, d, 7.3 Hz, H$_3$-25), 1.25 (1H, ddd, 4.4, 8.8, 13.8 Hz, H-20), 1.25 (3H, s, H$_3$-27), 1.40 (1H, m, H-21), 1.80 (1H, ddd, 4.4, 8.7, 13.8 Hz, H-20), 1.82 (1H, m, H-18), 1.90 (1H, bRt, 12.3 Hz, H-10), 1.96 (1H, dt, 14.1, 11.6 Hz, H-17), 2.15 (1H, m, H-17), 2.12 (3H, s, H$_3$-24), 2.18 (2H, m, H$_2$-8), 2.21 (1H, brd, 12.7 Hz, H-10), 2.26 (1H, brd, 13.6 Hz, H-12), 2.40 (1H, d, 13.6 Hz, H-12), 2.46 (1H, dq, 2.9, 7.3 Hz, H-4), 3.52 (1H, brd, 1.9 Hz, 13-OH), 3.58 (1H, quint, 6.3 Hz, H-22), 3.81 (1H, bRt, 11.5 Hz, H-9), 4.28 (1H, brs, H-5), 4.82 (2H, brs, H$_2$-26), 5.11 (1H, m, H-19), 5.57 (1H, dd, 4.1, 15.7 Hz, H-6), 5.68 (1H, m, H-7), 5.72 (1H, brs, H-2), 5.68 (1H, brd, 15.5 Hz, H-15), 5.76 (1H, ddd, 3.1, 10.8, 15.5 Hz, H-16), $^{13}$C-NMR spectrum (150 MHz in deuterated chloroform) δ 14.2 (CH$_3$, C-28), 15.5 (CH$_3$, C-29), 15.6 (CH$_3$, C-25), 19.8 (CH$_3$, C-23), 23.1 (CH$_3$, C-27), 23.8 (CH$_3$, C-24), 36.5 (CH$_2$, C-20), 36.5 (CH, C-21), 36.88 (CH$_2$, C-12), 36.94 (CH, C18), 38.2 (CH$_2$, C-17), 39.5 (CH$_2$, C-8), 40.7 (CH$_2$, C-10), 47.9 (CH, C-4), 70.8 (CH, C-19), 71.8 (CH, C-9), 72.2 (CH, C-22), 72.3 (CH, C-5), 77.2 (C, C-14), 99.7 (C, C-13), 110.6 (CH$_2$, C-26), 115.8 (CH, C-2), 126.8 (CH, C-7), 128.8 (CH, C-16), 132.0 (CH, C-6), 134.9 (CH, C-15), 141.7 (C, C-11), 162.0 (C, C-3), 167.4 (C, C-1)

d) A compound represented by Formula 9: $R_1$, $R_2$, $R_3$ and $R_4$ are each hydrogen in Formula 3.

[Compound 14]

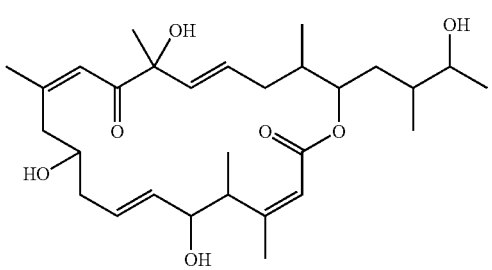

Formula 9

Form: colorless solid, solubility: soluble in chloroform, acetone, ethyl acetate and ethanol, insoluble in water and hexane, molecular weight measurement: m/z 529.2 (M+Na)$^+$, $^1$H-NMR spectrum (600 MHz in deuterated chloroform) δ 0.87 (3H, d, 6.7 Hz, H$_3$-29), 0.90 (3H, d, 6.8 Hz, H$_3$-28), 1.13 (1H, m, H-20), 1.13 (3H, d, 6.3 Hz, H$_3$-23), 1.18 (3H, d, 7.3 Hz, H$_3$-25) 1.44 (3H, s, H$_3$-27), 1.45 (1H, m, H-21), 1.72 (1H, m, H-18), 1.75 (1H, m, H-17), 1.76 (1H, m, H-20), 2.08 (1H, m, H-8), 2.17 (3H, s, H$_3$-26), 2.20 (3H, s, H$_3$-24), 2.23 (1H, bRt, 12.3 Hz, H-10), 2.24 (1H, m, H-17), 2.28 (1H, brd, 12.7 Hz, H-10), 2.30 (1H, m, H-8), 2.62 (1H, dq, 2.9, 7.3 Hz, H-4), 3.61 (1H, m, H-22), 3.72 (1H, m, H-9), 4.33 (1H, brs, 14-OH, H-14) 4.46 (1H, dd, H-5), 4.92 (1H, dt, H-19), 5.56 (1H, m, H-6), 5.56 (1H, m, H-7), 5.58 (1H, d, 15.6 Hz, H-15), 5.63 (1H, brs, H-2), 5.74 (1H, dt, 15.5 Hz, H-16), 6.18 (1H, s, H-12), $^{13}$C-NMR spectrum (150 MHz in deuterated chloroform) δ 11.2 (CH$_3$, C-25), 14.6 (CH$_3$, C-28), 14.8 (CH$_3$, C-29), 19.7 (CH$_3$, C-23), 20.0 (CH$_3$, C-26), 20.4 (CH$_3$, C-24), 25.2 (CH$_3$, C-27), 32.4 (CH$_2$, C-20), 34.7 (CH$_2$, C-17), 36.5 (CH, C-21), 37.2 (CH, C18), 40.8 (CH$_2$, C-8), 48.6 (CH$_2$, C-10), 48.7 (CH, C-4), 68.3 (CH, C-9), 72.8 (CH, C-5), 72.2 (CH, C-22), 74.7 (CH, C-19), 77.9 (C, C-14), 116.2 (CH, C-2), 121.8 (CH, C-12), 129.6 (CH, C-6), 130.4 (CH, C-16), 132.4 (CH, C-7), 133.2 (CH, C-15), 157.5 (C, C-11), 160.8 (C, C-3), 166.7 (C, C-1), 200.8 (C, C-13)

e) A compound represented by Formula 10: R$_1$, R$_2$, and R$_3$ are each hydrogen in Formula 4.

[Compound 15]

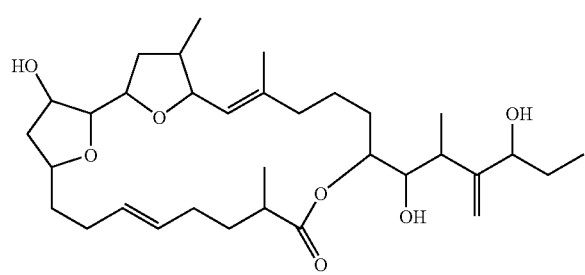

Formula 10

Form: colorless solid, solubility: soluble in chloroform, acetone, ethyl acetate and ethanol, insoluble in water and hexane, molecular weight measurement: m/z 585.4 (M+Na)$^+$, $^1$H-NMR spectrum (600 MHz in deuterated chloroform) δ 0.86 (3H, t, 7.0 Hz, H$_3$-28), 0.98 (3H, d, 6.7 Hz, H$_3$-30), 1.08 (3H, d, 7.0 Hz, H$_3$-32), 1.12 (3H, d, 7.2 Hz, H$_3$-29), 1.34 (1H, m, H-20), 1.41 (1H, m, H-3), 1.42 (1H, m, H-27), 1.43 (1H, m, H-20), 1.45 (1H, m, H-21), 1.57 (1H, m, H-8), 1.63 (1H, m, H-27), 1.67 (3H, s, H$_3$-31), 1.70 (1H, m, H-14), 1.71 (1H, m, H-10), 1.76 (1H, m, H-3), 1.82 (1H, m, H-21), 1.83 (1H, m, H-8), 1.90 (1H, m, H-4), 1.95 (2H, m, H$_2$-19), 2.04 (1H, m, H-7), 2.04 (1H, m, H-4), 2.06 (1H, m, H-15), 2.15 (1H, m, H-14), 2.19 (1H, m, H-7), 2.20 (1H, m, H-10), 2.43 (1H, m, H-24), 2.44 (1H, m, H-2), 3.60 (1H, dd, 2.0, 9.4 Hz, H-23), 3.71 (1H, m, H-12), 3.94 (1H, m, H-9), 3.98 (1H, t, 7.6 Hz, H-26), 4.07 (1H, t, 3.4 Hz, H-16), 4.41 (1H, m, H-11), 4.42 (1H, m, H-13), 5.00 (1H, s, H-33), 5.03 (1H, brd, 8.2 Hz, H-22), 5.07 (1H, s, H-33), 5.09 (1H, d, 3.4 Hz, H-17), 5.34 (1H, m, H-5), 5.46 (1H, dt, 15.0 Hz, H6), $^{13}$C-NMR spectrum (150 MHz in deuterated chloroform) δ 10.2 (CH$_3$, C-28), 16.0 (CH$_3$, C-29), 16.7 (CH$_3$, C-30), 17.2 (CH$_3$, C-31), 17.8 (CH$_3$, C-32), 24.7 (CH$_2$, C-20), 26.5 (CH$_2$, C-21), 28.7 (CH$_2$, C-7), 29.1 (CH$_2$, C-27), 29.5 (CH$_2$, C-4), 33.2 (CH$_2$, C-3), 35.6 (CH, C-24), 36.3 (CH$_2$, C-14), 36.5 (CH$_2$, C-8), 37.6 (CH, C-2), 39.7 (CH$_2$, C-19), 39.8 (CH, C-15), 41.4 (CH$_2$, C-10), 72.8 (CH, C-11), 75.1 (CH, C-22), 78.4 (CH, C-23), 77.2 (CH, C-26), 77.5 (CH—C-13), 77.6 (CH, C-9), 82.8 (CH, C-16), 83.1 (CH, C-12), 112.4 (CH$_2$, C-33), 124.1 (CH, C-17), 129.1 (CH, C-5), 131.2, (CH, C-6), 141.5 (C, C18), 153.9 (C, C-25), 176.6 (C, C-1)

f) A compound represented by Formula 11: R$_1$, R$_2$, and R$_3$ are each hydrogen in Formula 5.

[Compound 16]

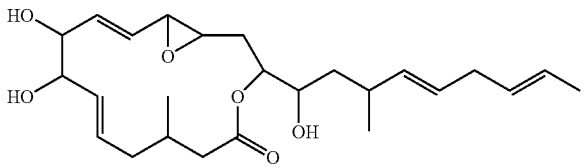

Formula 11

Form: colorless solid, solubility: soluble in chloroform, acetone, ethyl acetate and ethanol, insoluble in water and hexane, molecular weight measurement: m/z 457.2 (M+Na)$^+$, $^1$H-NMR spectrum (600 MHz in deuterated chloroform) δ 1.01 (3H, d, 7.3 Hz, H$_3$-24), 1.01 (3H, d, 7.3 Hz, H$_3$-25), 1.27 (1H, m, H-16), 1.39 (1H, ddd, 2.0, 9.3, 15.5 Hz, H-16), 1.48 (1H, dt, 14.3, 9.8 Hz, H-13), 1.64 (3H, d, 4.2 Hz, H$_3$-23), 1.82 (1H, m, H-4), 1.98 (1H, dd, 6.8, 14.0 Hz, H-2), 2.10 (1H, m, H-3), 2.26 (1H, brd, 14.3 Hz, H-13), 2.32 (1H, m, H-4), 2.35 (1H, m, H-17), 2.38 (1H, dd, 2.4, 14.0 Hz, H-2), 2.40 (1H, brd, 8.7 Hz, H-12), 2.66 (2H, ddd, 4.4, 8.7, 13.8 Hz, H$_2$-20), 3.00 (1H, brd, 9.8 Hz, H-11), 3.60 (1H, m, H-15), 3.96 (1H, m, H-7), 3.96 (1H, m, H-8), 5.11 (1H, brd, 9.8 Hz, H-14), 5.20 (1H, dd, 8.0, 15.2 Hz, H-18), 5.24 (1H, dd, 9.8, 15.4 Hz, H-10), 5.38 (1H, m, H-21), 5.40 (1H, m, H-6), 5.40 (1H, m, H-22), 5.45 (1H, m, H-19), 5.77 (1H, m, H-5), 5.79 (1H, m, H-9), $^{13}$C-NMR spectrum (150 MHz in deuterated chloroform) δ 17.8 (CH$_3$, C-23), 20.7 (CH$_3$, C-24), 21.6 (CH$_3$, C-25), 29.8 (CH, C-3), 33.3 (CH, C-17), 34.3 (CH$_2$, C-13), 35.4 (CH$_2$, C-20), 36.0 (CH$_2$, C-4), 37.7 (CH$_2$—C-2), 40.6 (CH$_2$, C-16), 57.7 (CH, C-12), 59.0 (CH, C-11), 70.8 (CH, C-15), 72.7 (CH, C-14), 76.6 (CH, C-8), 76.7 (CH, C-7), 125.6 (CH, C-22), 128.6 (CH, C-19), 129.5 (CH, C-21), 131.3 (CH, C-6), 132.5 (CH, C-10), 133.2 (CH, C-5), 135.3 (CH, C18), 135.8 (CH, C-9), 172.6 (C, C-1)

It was found that 2 types of *dinoflagellate* algae that produce the macrolide compound in this invention are novel *dinoflagellate* algae identified as *Amphidinium* sp. Strain HYA002 and HYA024, which were isolated from *platyhelminth Amphiscolops* sp. in vivo collected at Chatan Town of Okinawa Prefecture and from seawater of Iriomote (an island) of Okinawa Prefecture, respectively. *Dinoflagellate* alga Strains HYA002 and HYA024 of this invention are preserved at the Department of Natural Products Chemistry, Graduate School of Pharmaceutical Sciences, Hokkaido University and Center for Advanced Marine Core Research, Kochi University.

A macrolide compound in this invention can be obtained by culturing *dinoflagellate* alga Strain HYA002 or HYA024 under an appropriate condition. For example, a seawater-fortified nutrient having compositions as shown in the following Table 1 is added to seawater autoclave-sterilized at 120° C. for 20 minutes so as to set the concentration at 1%. Then, after 3 mM $NaHCO_3$ is added thereto with a pH ranging from 7.3 to 8.5, *dinoflagellate* alga Strains HYA002 and/or HYA024 are inoculated in a culture solution prepared by filter sterilization using a filter with a pore diameter of 0.22 µm, and may be allowed to stand for culturing at 25° C. for approx. 14 days, irradiated with 3000 lux light during one cycle, composed of 16 hours in light time period and 8 hours in dark time period.

TABLE 1

Compositions in seawater-fortified nutrient;

| | |
|---|---|
| $H_2O$ | 1393.5 ml |
| 1% $Na_2$EDTA Solution | 45 ml |
| 0.1% $FeCl_3$ Solution | 41.25 ml |
| 4% $MnCl_2$, 0.5% $ZnCl_2$, 0.1% $CoCl_2$ Solution | 0.375 ml |
| $NaNO_3$ | 5.25 g |
| $Na_2$ glycerophosphoric acid | 0.75 g |
| 2% $H_3BO_4$ Solution | 3.75 ml |
| 0.001% vitamin $B_{12}$ Solution | 15 ml |
| 1% thiamine HCl Solution | 0.75 ml |
| 0.01% biotin | 0.75 ml |
| Tris | 7.5 g |

However, the culture conditions such as culture solution composition or temperature are not limited in this invention and can obviously be adjusted or selected accordingly.

In view of physicochemical properties of the macrolide compound, the macrolide compound which has been produced and accumulated in a culture solution may be collected by separation and refinement means accordingly, which are commonly used in collecting metabolite, for culture algae obtained by centrifugal separation or filtration. For example, culture algae are extracted using a solvent like methanol, preferably methanol/toluene (3:1), and a macrolide compound is extracted from an extract (toluene fraction) obtained using an organic solvent like dichloromethane, or column chromatography method may adsorb and elute a macrolide compound. The product can be furthermore refined as needed to collect and produce a macrolide compound having a desired purity. A carrier used in chromatography is conventionally-used inorganic or organic carrier, e.g. silica gel, polyvinyl resin or polystyrene resin.

A macrolide compound in this invention is useful as, e.g. an anticancer agent in the field of medicines. The compound in this invention may be used alone or blended or formulated in combination with a generally allowable inorganic or organic medicine, or several vehicles, carriers, excipients, disintegrants, binders, brighteners, preservatives, stabilizers, humectants, suspension auxiliary agents, edulcorants, fragrances, coloring agents, etc.

Drug formulation may be appropriately determined according to route of administration, dosing regimen, etc. Dosage forms include oral, enteral, parenteral and topical administration. Parenteral administration includes intravenous, intramuscular and subcutaneous administration using parenteral injection. Based on conventionally known technologies, a drug can be formulated in granule, fine granule, powder medicine, tablet, hard capsule, soft capsule, syrup, emulsion, suspending agent, liquid medicine, etc. When solid preparations such as powder medicine, tablet, granule and capsule are produced, a macrolide compound of this invention can be blended in combination with binder like corn starch, gelatin and dextrin, excipient like kaolin, calcium carbonate and microcrystalline cellulose, disintegrant like starch and carboxymethylcellulose sodium, brightener like talc and edulcorant like lactose and sucrose. When liquid preparations such as emulsion, syrup, suspending agent and liquid medicine are produced, a macrolide compound of this invention can be blended in combination with humectant, suspension auxiliary agent, edulcorant, coloring agent, preservative, stabilizer, etc., in addition to generally used inactive diluent like water and plant oil.

Solvents or suspending agents used in producing parenterally administered drugs like parenteral injection include water, propylene glycol, polyethylene glycol, benzyl alcohol, ethyl oleate and lecithin.

A clinical dose of a macrolide compound of this invention is approx. 0.1 to 100 mg for an adult in oral administration, preferably 1 to 10 mg, but more preferably is appropriately adjusted according to patient's age, condition, symptom and simultaneous administration with other drugs.

EXAMPLES

Example 1

A seawater-fortified nutrient having compositions as shown in the above Table 1 was added to seawater autoclave-sterilized at 120° C. for 20 minutes so as to set the concentration at 1%. Then, after 3 mM $NaHCO_3$ was added thereto with a pH ranging from 7.3 to 8.5, *dinoflagellate* alga Strains HYA002 and/or HYA024 were inoculated in a culture solution prepared by filter sterilization using a filter with a pore diameter of 0.22 µm. The product was allowed to stand for culturing at 25° C. for approx. 14 days, irradiated with 3000 lux light during one cycle, composed of 16 hours in light time period and 8 hours in dark time period.

Subsequently, 200 mL of methanol/toluene (3:1) was added to 60.5 g of *dinoflagellate* alga collected by centrifugal separation and the product was agitated (3 times). Thereafter, 100 mL of 1M NaCl was added thereto and culture algae were extracted with 100 mL of toluene 3 times. All toluene fractions (730 mg) were put in a silica gel column (eluate: $CHCl_3$/MeOH) and refined with Sep-Pak C18 column (MeOH as eluate:water=8:2) and then YMC-Pack PRO C18 column (YMC Co., Ltd., acetonitrile as eluate/water=75:25, flow rate: 3 mL/min, detection: UV210 nm) to separate and collect 6 types of candidate macrolide compounds.

High-resolution electrospray ionization mass spectrometry (HRESIMS) was performed to find out the molecular weights in the 6 types of compounds obtained. Also, spectrum data were measured mainly based on nuclear magnetic resonance (NMR) to define chemical structure formulae for the 6 types of compounds as Formula 6, Formula 7, Formula 8, Formula 9, Formula 10 and Formula 11.

[Compound 17]

Formula 6

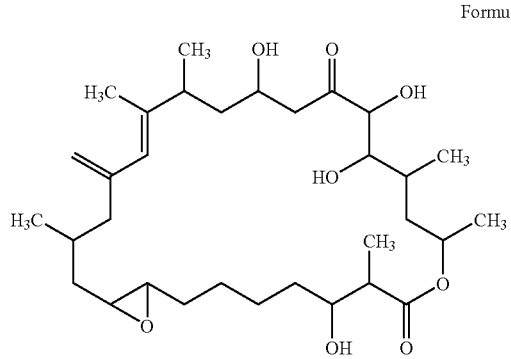

High-resolution electrospray ionization mass spectrometry (HRESIMS) (m/z 589.3718 ([M+Na]$^+$))

Molecular weight (C32H54O8Na, calculated value: 589.3716)

[Compound 18]

Formula 7

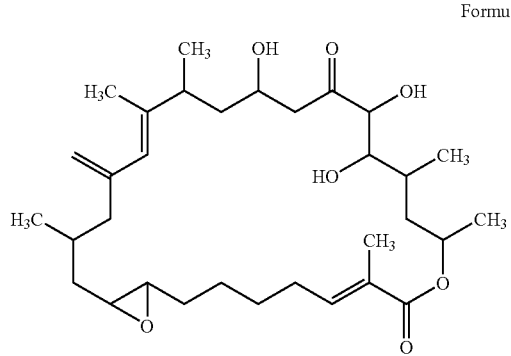

High-resolution electrospray ionization mass spectrometry (HRESIMS) (m/z 571.3621 ([M+Na]$^+$))

Molecular weight (C32H52O7Na, calculated value: 571.3611)

[Compound 19]

Formula 8

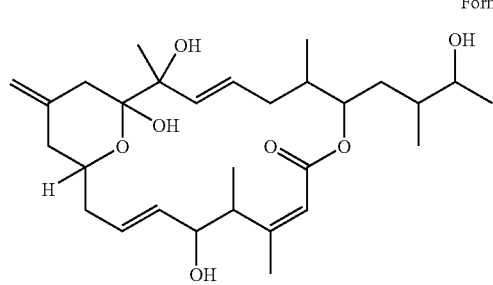

High-resolution electrospray ionization mass spectrometry (HRESIMS) (m/z 529.3148 ([M+Na]$^+$))

Molecular weight (C29H46O7Na, calculated value: 529.3141)

[Compound 20]

Formula 9

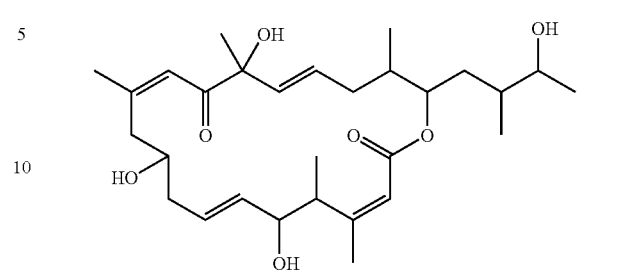

High-resolution electrospray ionization mass spectrometry (HRESIMS) (m/z 529.3145 ([M+Na]$^+$))

Molecular weight (C29H46O7Na, calculated value: 529.3141)

[Compound 21]

Formula 10

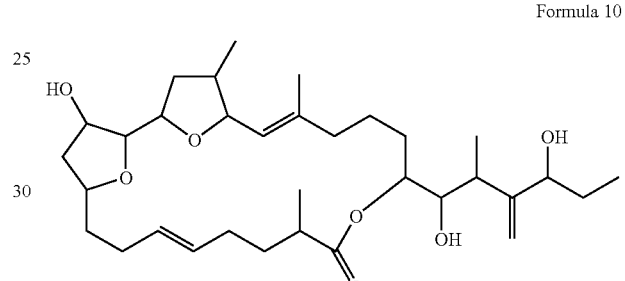

High-resolution electrospray ionization mass spectrometry (HRESIMS) (m/z 585.3749 ([M+Na]$^+$))

Molecular weight (C33H54O7Na, calculated value: 585.3767)

[Compound 22]

Formula 11

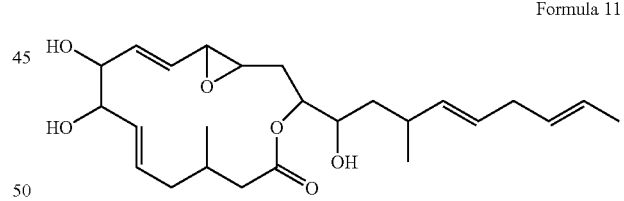

High-resolution electrospray ionization mass spectrometry (HRESIMS) (m/z 457.2566 ([M+Na]$^+$))

Molecular weight (C25H38O6Na, calculated value: 457.2566)

Formula 11

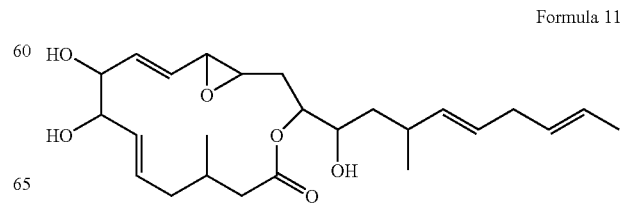

Example 2

Human BuRkitt's lymphoma cell line (DG-75, ATCC No. CRL-2675) or human Burkitt's lymphoma cell line (Raji, ATCC No. CRL-86) was suspended in an RPMI-1640 medium (SIGMA) (hereinafter called culture solution) containing 10% calf serum (Moregate) and 10% fetal bovine serum (Hyclone) so as to set the cell number at $1\times10^5/mL$. After 50 μL of the cell suspension was added to a 96-well microplate, 49 μL of the above culture solution was added thereto to set the whole volume at 99 μL. Compounds represented by Formulae (6) to (11) that solved in DMSO, 5-FU (Wako) or doxorubicin (Wako) (all 0.0001 to 10 μg/mL) were each added to one well by 1 μL, and cultured with a $CO_2$ concentration of 5% at 37° C. for 72 hours. After culturing, 10 μL of Wako cell Counting Kit-8 (Wako) was added to each well and subjected to color reaction in a $CO_2$ incubator for 3 hours. Proliferation-inhibition rate was calculated from absorbance values measured with a microplate reader at 450 nm (reference wavelength: 620 nm) using the following expression to determine a compound concentration in a culture solution with a proliferation-inhibition rate of 50% as $IC_{50}$ value.

Proliferation-inhibition rate (%)=(1−(sample/blank))× 100

Table 2 shows $IC_{50}$ values for each novel macrolide compound and existing anticancer agent.

TABLE 2

|  | DG-75 | (Unit μg/mL) Raji |
|---|---|---|
| Compound 6 | 0.02 | — |
| Compound 7 | 0.4 | — |
| Compound 8 | 0.002 | 0.003 |
| Compound 9 | 0.9 | — |
| Compound 10 | 0.006 | 0.01 |
| Compound 11 | 0.08 | 0.05 |
| 5-FU | 0.9 | 3.0 |
| Doxorubicin | 0.04 | 0.02 |

From these observations, it was confirmed that a novel macrolide compound can be an excellent anticancer agent having a high antitumor activity.

Example 3

A compound represented by Formula (8) (50 to 500 μg/kg) that solved in ethanol or 5-FU (10 mg/kg) was administered to an 8-week old female Balb/c mouse (Japan SLC) having approx. $1\times10^5$ of Meth A fibrosarcoma cells (Kitasato Institute) intraperitoneally transplanted therein by ⅓ of the whole volume at 7th, 9th and 11th days intravenously (but 5-FU administered intraperitoneally) to measure tumor weight at 21st day. Using a control mouse to which normal saline solution was administered in lieu of a test compound, anticancer activity on each compound was expressed in number according to a formula of proliferation-inhibition rate (%)= (1−(sample/blank))×100. Table 3 shows the results.

TABLE 3

|  | Concentration (μg/kg) | Proliferation-inhihition rate (%) |
|---|---|---|
| Formula (8) | 50 | 5.3 |
|  | 200 | 62.2 |
|  | 500 | 54.3 |
| 5-FU | 10000 | 60.2 |

The above test found that the compound represented by Formula (8) shows almost the same proliferation-inhibition rate (anticancer activity) as 5-FU even when it is administered with a lower concentration.

The invention claimed is:
1. A compound consisting of at least one of following general Formula 1, Formula 2, Formula 3, Formula 4 and Formula 5 and salts thereof:

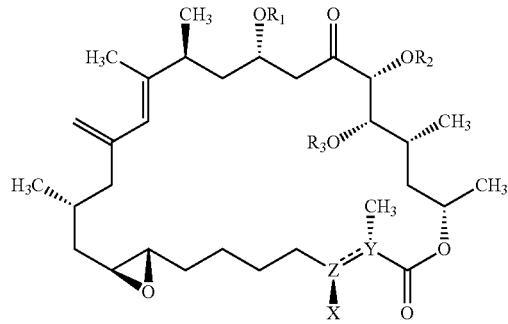

Formula 1

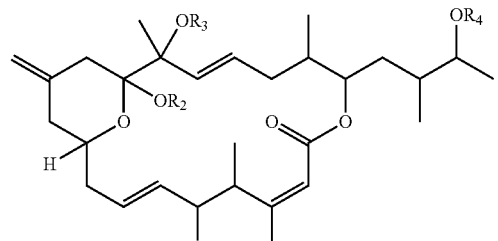

Formula 2

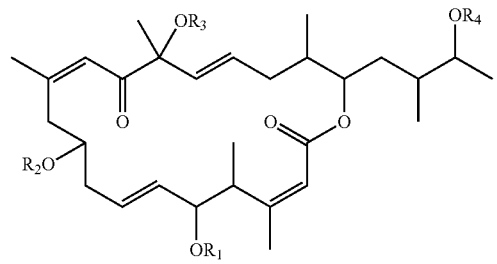

Formula 3

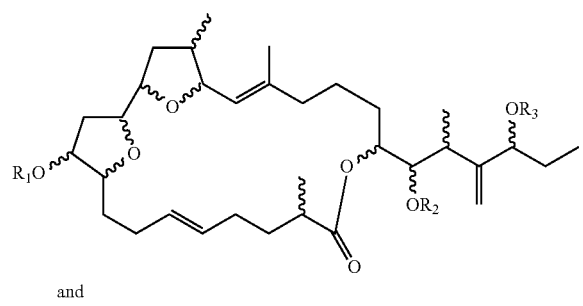

Formula 4 and

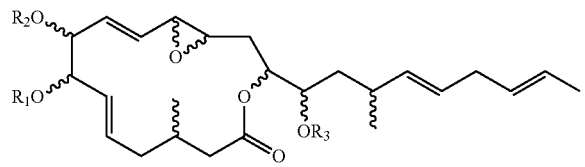

Formula 5 wherein R1, R2, R3 and R4 are respectively a hydrogen carbon group; Z-Y is one selected from a carbon single bond and a carbon double bond; and wherein, when Z-Y is a carbon single bond, X is hydroxy group, and when Z-Y is a carbon double bond, X is hydrogen; and wherein any one of compounds of said Formulae 1 to 5 is made by a process for culturing an *Amphidinium* sp. Strain HYA002 as a *dinoflagellate* alga, and a process for collecting at least one of compounds of said Formulae 1 to 5 from the culture.

2. An anticancer agent containing at least one of compounds set forth in claim 1 as an active ingredient.

3. A method for producing any one of compounds consisting of at least one of following general Formula 1, Formula 2, Formula 3, Formula 4 and Formula 5 and salts thereof:

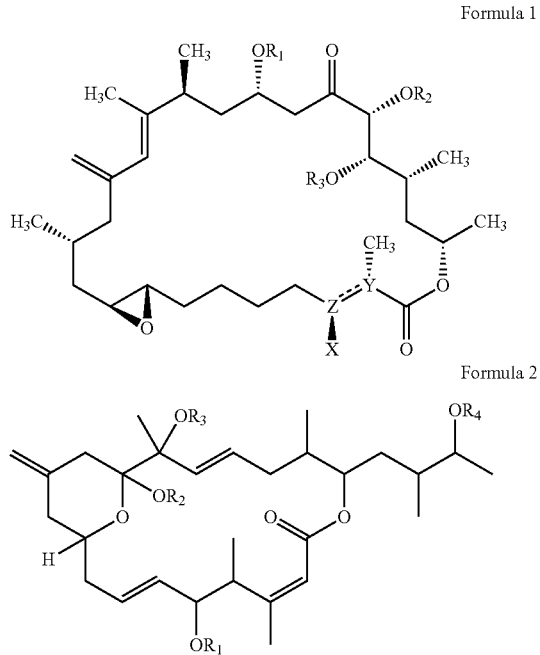

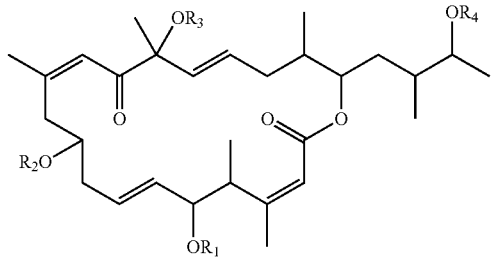

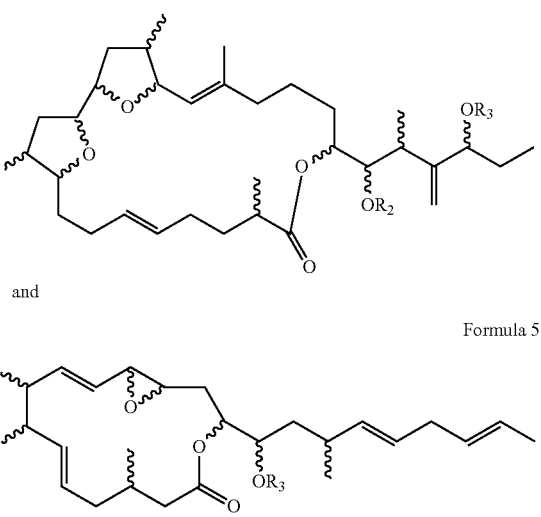

wherein $R_1$, $R_2$, $R_3$ and $R_4$ are respectively a hydrogen group; Z-Y is one selected from a carbon single bond and a carbon double bond; and wherein, when Z-Y is a carbon single bond, X is hydroxy group, and when Z-Y is a carbon double bond, X is hydrogen, said method comprising a process for culturing an *Amphidinium* sp. Strain HYA024 as a dinoflagellate alga, and a process for collecting at least one of compounds of said Formulae 1 to 5 from the culture.

* * * * *